United States Patent [19]

Yoshida et al.

[11] Patent Number: 4,571,334
[45] Date of Patent: Feb. 18, 1986

[54] COMPOSITION FOR CURING RESPIRATORY DISEASES

[75] Inventors: Tsunemasa Yoshida; Toshio Wakabayashi, both of Tokyo; Keizo Matsumoto, Nagasaki, all of Japan

[73] Assignee: Teijin Limited, Osaka, Japan

[21] Appl. No.: 327,396

[22] Filed: Dec. 4, 1981

[30] Foreign Application Priority Data

Dec. 4, 1980 [JP] Japan .................. 55-170222

[51] Int. Cl.⁴ .................. A61K 31/395; A61K 35/12
[52] U.S. Cl. .................. 424/95; 514/200
[58] Field of Search .................. 424/95, 246

[56] References Cited

U.S. PATENT DOCUMENTS 4,243,582  1/1981  Spelburg et al. .................. 424/95

Primary Examiner—Elbert L. Roberts
Attorney, Agent, or Firm—Sughrue, Mion, Zinn, Macpeak and Seas

[57] ABSTRACT

A composition for curing respiratory diseases which contains a medicine such as antibiotic, chemotherapeutic and anticancer drug for respiratory disease and lung surfactant.

8 Claims, 3 Drawing Figures

COMPOSITION FOR CURING RESPIRATORY DISEASES

BACKGROUND OF THE INVENTION

The present invention relates to a composition, which contains a lung surfactant, for curing respiratory diseases.

As drugs for curing respiratory diseases, there are such antagonizers as antibiotics and chemotherapeutics besides antitussives, expectorants, bronchodilators, antiallergic drugs, antiinflammatory drug, anticancer drugs, etc. These medicines for curing respiratory diseases are used by general administration such as oral administration, intraveneous injection, intramuscular injection, etc.; however, in the case of some therapeutic medicines, especially antagonizers and antiallergic drugs like antasthmatics, the administration by means of inhalation or infusion is also adopted.

The administration of a drug by inhalation or infusion is what is called a local treatment effected by a direct application of a drug to the affected part and can be expected to produce less side effects as compared with the general administration of a drug mentioned above. However, the application of a drug by inhalation or infusion to the respiratory apparatus inclusive of naris, throat, trachea, lung, etc. sometimes results in the insufficient absorption of the drug through the mucous membrane depending upon the drug, thus it is at a disadvantage in being unable to achieve enough indirect remedial effect attributable to the increase of the concentration of the drug in the blood. Some drugs make it impracticable to administer the drug by inhalation or infusion as they irritate the mucous membrane of the respiratory tracts of the bronchi, etc. causing the emission of coughs.

On the other hand, the lung surfactant protects the respiratory epitheria by covering the inner walls of the alveoli of lung and also has a physiological function which is important for the animals to maintain their respiratory function properly. More particularly, the lung surfactant has a singular surface activity which makes the surface tension of the inner surface of the alveolium vary in accordance with the expiration and inspiration and contributes to the maintenance of interalveolium functional stabilization to exercise an antiatelectatic action. It is known that this surfactant contains phospholipids, neutral lipids, protein, etc. as ingredients and has dipalmitoyl lecithin as a main ingredient. T. Fujiwara et al. recently reported that they obtained an artifically prepared lung surfactant having a higher surface activity by adding dipalmitoyl lecithin, etc. to a surfactant recovered from the bovine lung and that they achieved a good result for the therapy of indiopathic respiratory distress syndrome (IRDS) by the instillation of the said lung surfactant dispersion to the respiratory tracts of the premature babies (Pediatric Clinics, Vol. 32, No. 7, p.1335, 1979).

SUMMARY OF THE INVENTION

The inventors of this invention have come to know that, in the course of the strenuous research work to find out how to increase the absorption of a drug through the mucous membrane of the respiratory apparatus, improve the dispersibility of a drug to the peripheral airways and alveoli, or allay the irritation of the mucous membrane caused by a drug, a combined use of such a drug and lung surfactant enhances the absorption and mitigates the irritation of the membrane.

Accordingly the present invention is directed to a composition for curing respiratory diseases, which contains a medicine for respiratory disease and lung surfactant.

DESCRIPTION OF THE PREFERRED EMBODIMENT

Figure 1:
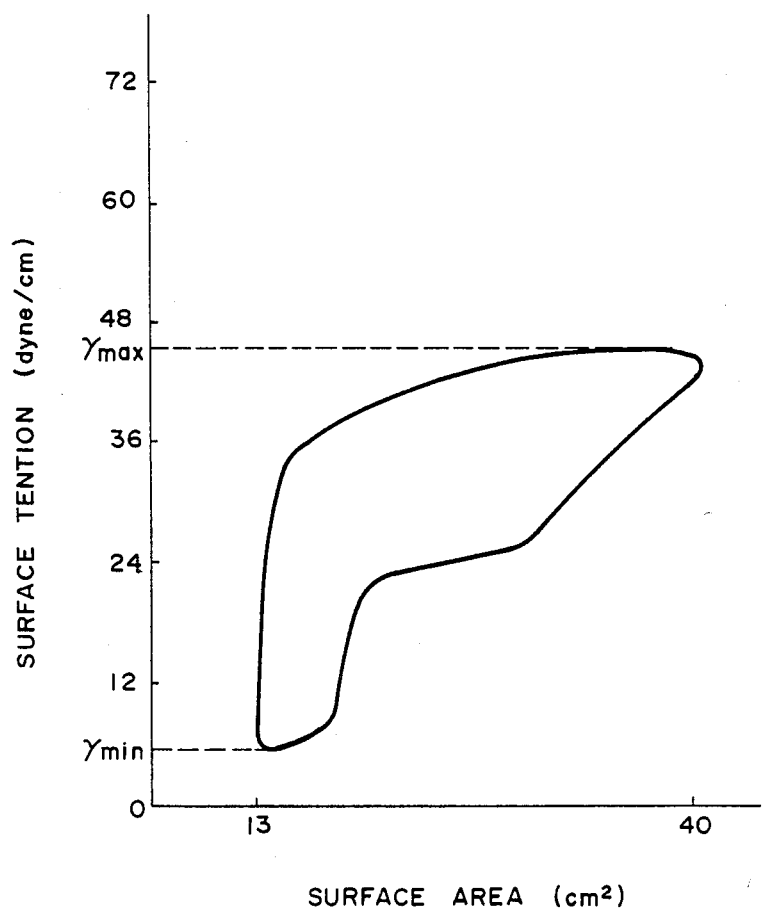
FIG. 1 shows a diagram of surface tension of lung surfactant verious surface area.

As the medicine for respiratory disease to be used in the present invention, there are such chemotherapeutics and antibiotics as antagonizers, anticancer drugs and such antasthatics as antiallergics, bronchodilator, antitussives, etc.

Accordingly, any of the medicines for respiratory disease can be used so far as they can be expected of medical efficacy when they are directly administered by inhalation or infusion to naris, throat, bronchial tube, respiratory tract, alveolium, etc.; however, it is desirable to use such ones that will not substantially react with the lung surfactant or that will not reciprocally or unilaterally degrade the pharmaceutical activity or physiological activity when they are made to coexist in a state of mixture. As concrete examples of desirable medicine, chemotherapeutic includes sulfonamide having an isoxazole nucleus such as sulfamethoxazole, etc., sulfonamide having a pyrimidine nucleus such as sulfadimethoxine, etc., sulfonamide having a pyrazole nucleus such as sulfaphenazole, etc., and antituberculotic such as PAS, INAH, etc.

As antibiotics, there are antibiotics of penicillin type such as amoxicillin, ampicillin, ciclacillin, carbenicillin, talanpicillin, benzylpenicillin, etc., antibiotics of cephalosporin type such as cephalexin, cephaloglycin, cefradine, cefazolin, cephalothin, etc., antibiotics of aminoglucoside type such as gentamicin sulfate, amikacin sulfate, etc., antibiotics of macrolide type such as erythromycin, oleandmycin, etc., antibiotics of tetracycline type such as minocycline, tetracycline, etc., and mitomycin C having a high antitumor activity. Also, anticancer drugs aimed for curing lung cancer, antiinflammatory drugs, antiallergic drugs, or immunoglobulins are desirable medicines.

As the lung surfactant to be used in the present invention, either natural or artificially prepared one may be used. The natural lung surfactant can be obtained by extraction from the washings or tissues of animal lung such as bovine lung, pig lung, etc.; however, since such surfactant has a possible hazard of containing lipoproteins originating from the respective animals, it is desirable to use a lung surfactant which has its proteins removed following the Folch procedure, etc. The artificial lung surfactant includes a semi-artificial lung surfactant prepared by adding such a specific ingredient as dipalmitol lecithin (DPL) and phosphatidyl glycerol (PG) to the natural lung surfactant base (see IRCS Medical Science, p.311, 1979) and an entirely artificial lung surfactant which is prepared, for instance, following the procedure of dissolving DPL and PG in chloroform, coprecipitating with acetone, and drying to obtain a powdery dry surfactant (see The Lancet, pp.64–68, January 10, 1981). In both cases, it is desirable to make the surfactant have the minimum surface tension of 20 dyne/cm or less when the surface activity is measured on a modified Wilhelmy balance and the stability index of 1.0 or more, which will be referred to later.

The constitution of the composition for curing respiratory diseases according to the present invention is 0.01 part by weight or more, preferably 0.1 to 100 parts by weight, of the lung surfactant against 1 part by weight of the drug. Besides the drug, the composition may contain a proper amount of an excipient, corrective, etc.

Since the composition for curing respiratory diseases of the present invention is administered to the diseased part mainly by inhalation or infusion, it is preferable to prepare it in the form of a fine powder or a dispersion liquid of water or a proper medium (ethanol, for instance). As the method for preparing a uniform dispersion liquid, there is one in which the medicine is firstly dissolved in distilled water or a saline solution when the medicine is water-soluble, or is thoroughly dispersed and suspended in water, etc. by means of ultrasonic wave or the like to make a dispersion liquid having particles of less than a few microns when the medicine in not water-soluble, and next a desired amount of a lung surfactant is added to thus prepared solution or dispersion liquid and obtain a homogeneous solution or dispersion liquid by means of ultrasonic wave, etc. A similarly homogeneous dispersion liquid can be prepared by adding a proper amount of distilled water or a saline solution to a mixture of a drug and lung surfactant with the use of ultrasonic wave, etc. Thus obtained dispersion liquid is administered by inhalation with use of a nebulizer, etc. or by infusion with use of a catheter, etc. For preservation's sake, the dispersion liquid can be once lyophilized and again dispersed in distilled water, etc. at the time of use to be administered by inhalation or infusion. In order to prepare a fine uniform medical powder, there is a method in which a medicine and lung surfactant are mixed thoroughly with a medically permissible proper excipient of fine powder, or a method in which the medicine and dry lung surfactant are mixed thoroughly. A fine medical powder can be administered with the use of a proper powder inhalator.

The lung surfactant which is used in the composition for curing respiratory diseases of the present invention not only has a functional efficacy to promote the absorption of the medicine for curing respiratory diseases through the respiratory membrane and increase the concentration of the medicine in the blood but also has a functional efficacy proper to the lung surfactant to assist the respiratory function of the lung. For instance, it is known that atelectasis is experienced in bacterial pneumonia, etc., which is said to be resulting from the degradation of lung surface activity. The administration of a medicine of the present invention consisting of an antagonizer and lung surfactant in such a case not only produces an effect of curing the infection with the increased concentration of the antagonizer in the blood but also supplies the highly active lung surfactant to make up for the decreased surface activity, thus meeting expectations of quick improvement of the disease.

The present invention is illustrated below with reference to the examples. The surface activity of the lung surfactant was determined according to the method mentioned below.

Determination of Surface Activity of Lung Surfactant and Calculation of Stability Index:

Lung surfactant was dispersed in distilled water in concentration of 1% by weight and was treated with ultrasonic waves to obtain a uniform dispersion liquid, which was then used as a test sample. A Whilhelmy blance of Acoma make was used in the measurement. 5 μl of said test sample was gently layered over 50 ml of saline solution in the teflon trough of the balance. The surface film area was compressed cyclically in the range of a maximum of 40 cm² to a minimum of 13 cm² at the rate of 0.3 cycle/min. to record a surface tension area diagram by use of an X-Y recorder. The minimum surface tension ($\gamma$ min) value and the maximum surface tension ($\gamma$ max) value were obtained from the hysteresis loop converged invariantly at the 5th or 6th cycling from the start (See FIG. 1). And the stability index (S.I.) was obtained from the following equation:

$$S.I. = 2(\gamma \max - \gamma \min)/\gamma \max + \gamma \min$$

EXAMPLE 1

3 kg of bovine lungs was homogenized with a saline solution, had its cellular debris removed, and was subjected to density gradient centrifugation to obtain crude lung surfactant. Thus obtained surfactant was dissolved in a solvent consisting of chloroform and methanol in a volume ratio of 2:1, from which undissolved substances were removed. The mixed solution was made to contact 0.5% saline solution by weight to remove protein (Folch procedure). Thereafter, the organic layer was collected and the solvents were removed to obtain about 3 g of white purified lung surfactant.

Its minimum surface tension ($\gamma$ min) was 5 dyne/cm and S.I. was 1.59.

800 mg of gentamicin sulfate was dissolved in 20 ml of water, to which 800 mg of the abovementioned lung surfactant was added -nd the mixture was treated with ultrasonic wave to give a homogeneous dispersion liquid.

Then, an experiment was conducted with the use of a group consisting of three (Japanese white) rabbits weighing approximately 3 kg. The anterior jugulum of each rabbit was cut open to expose the trachea, which was then punctured with an 18-gauge teflon sheath needle (70 cm long). The needle was further led through to the bronchus to infuse 2 ml of the dispersion liquid containing 80 mg of gentamicin sulfate and 80 mg of lung surfactant per rabbit. Blood samples were taken at regular intervals to measure the concentration of gentamicin sulfate in the serum. A control experiment was also conducted with a group of three similar rabbits. 2 ml of water containing 80 mg of gentamicin sulfate dissolved therein was infused to each rabbit according to the same method mentioned above and the concentration of gentamicin sulfate was measured.

Figure 2:
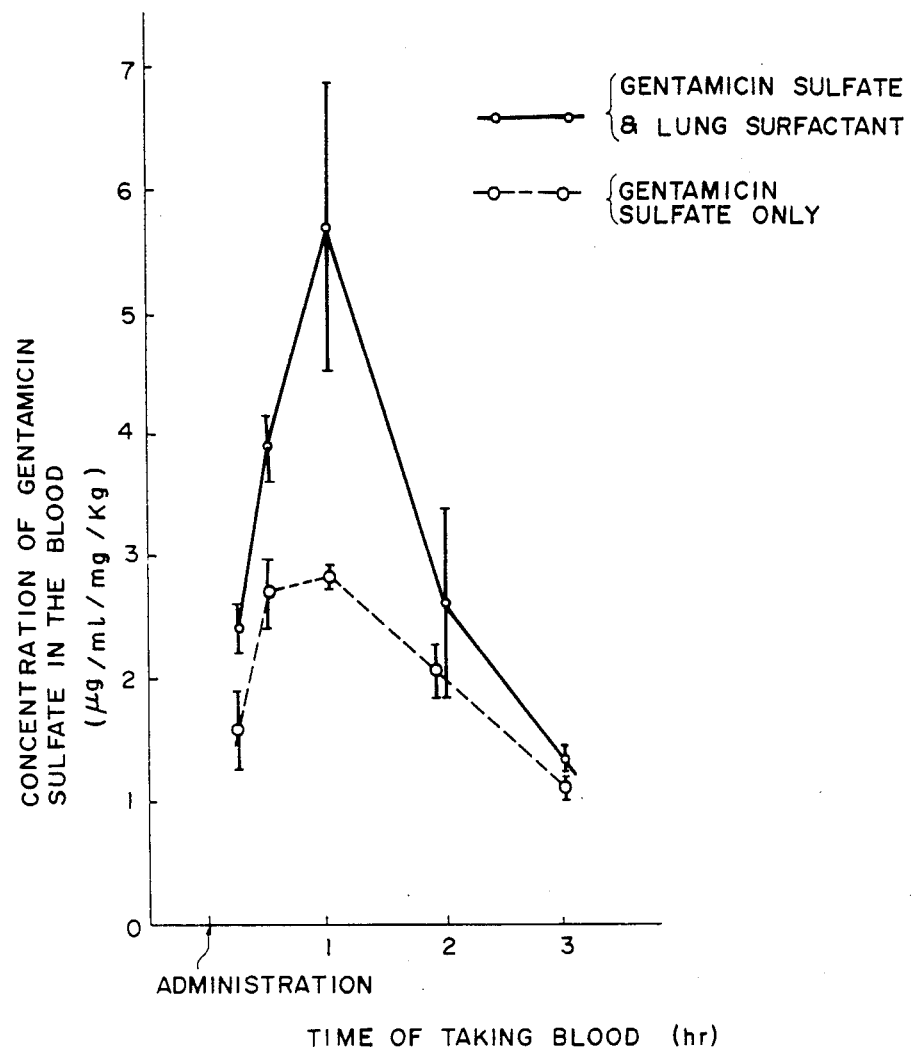
FIG. 2 shows the concentration of gentamicin sulfate in the blood changing as the time proceeds after the administration of the medicine for respiratory disease (gentamicin sulfate plus lung surfactant) of the present invention to rabbits.
Figure 3:
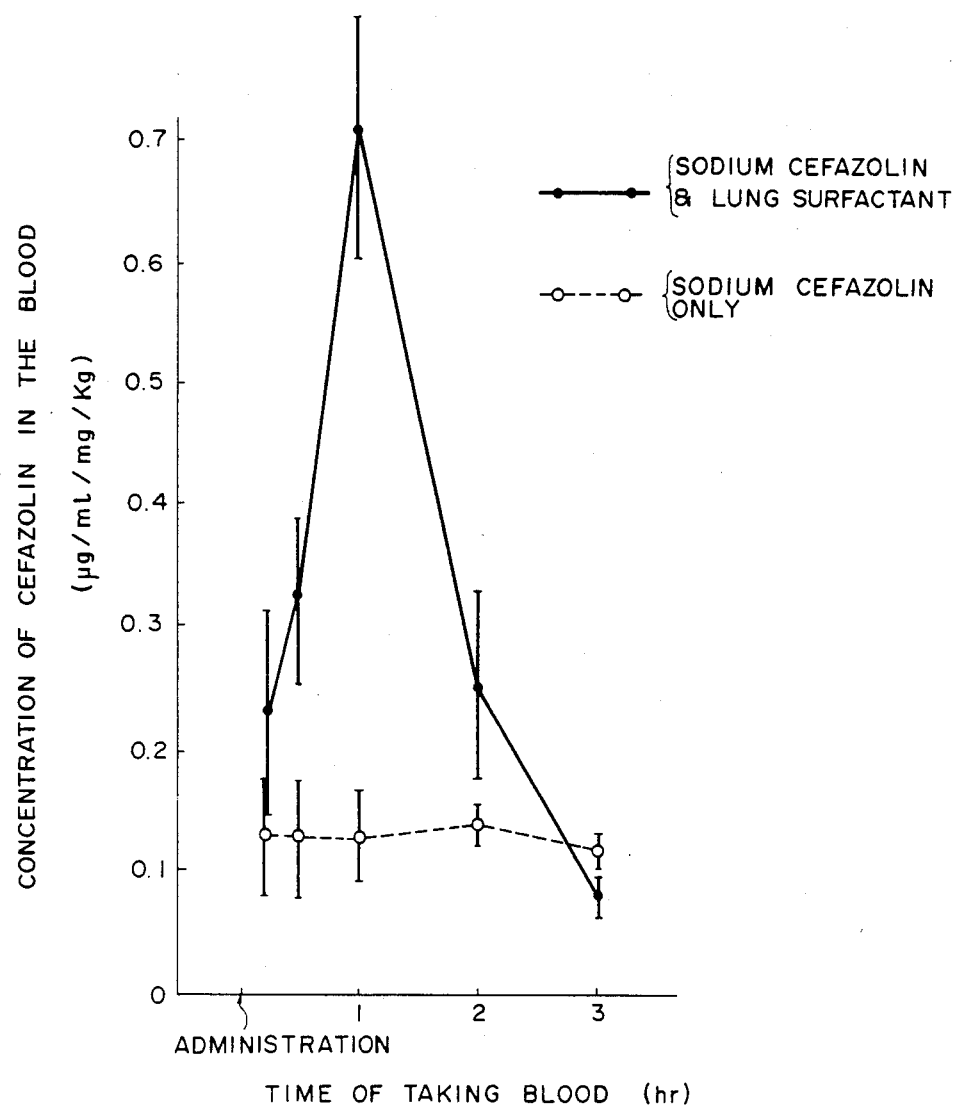
FIG. 3 shows the concentration of sodium cefazolin in the blood changing as the time proceeds after the administration of the medicine for respiratory disease (sodium cefazolin plus lung surfactant) of the present invention to rabbits.

The results of these experiments are shown in FIG. 2. In FIG. 2 and FIG. 3, the concentration of the medicine is shown by the absorption index (μg/ml/mg/kg) adjusted by the amount of the medicine administered per rabbit weight.

As clearly shown in FIG. 2, the concentration of the medicine in the blood is very high in the case where gentamicin sulfate is used in combination with lung surfactant as compared with the case where gentamicin sulfate is used alone.

When the observation was made as to the state of the rabbits administered with the medicine, it was inferred that the administration of gentamicin sulfate and lung surfactant together gave less stimulus to the membrane of bronchi than the administration of gentamicin sulfate alone from the fact that the former caused the rabbits to cough less often than the latter.

EXAMPLE 2

5.0 g of sodium cefazolin and 500 mg of lung surfactant obtained in Example 1 were added to 20 ml of water and were treated with ultrasonic wave to obtain a homogeneous dispursion liquid.

An experiment was conducted in the same way as Example 1, wherein a group consisting of three rabbits was used and each of them had an infusion of 2 ml of a dispersion liquid containing 500 mg of sodium cefazolin and 50 mg of lung surfactant. The blood was taken at regular intervals to measure the concentration of sodium cefazolin in the blood. A control experiment was conducted with a group consisting of three rabbits. Each of the rabbits was infused with 2 ml of an aqueous solution containing 500 mg of sodium cefazolin to measure its concentration in the blood. The results are shown in FIG. 3.

As clearly shown in FIG. 3, when sodium cefazolin is used together with lung surfactant, the concentration of sodium cefazolin in the blood is as high as two to five times as compared with its concentration when used alone. And the membrane of bronchi has less stimulus when sodium cefazolin was used together with lung surfactant.

EXAMPLE 3

50 mg of mitomycin C and 200 mg lung surfactant obtained in Example 1 were added to 25 ml of water and were treated with ultrasonic wave to obtain a homogeneous dispersion liquid.

An experiment was conducted in the same way as Example 1, wherein a group consisting of seven rabbits was used and each of them had an infusion of 3 ml of a dispersion liquid containing 6 mg of mitomycin C and 24 mg of lung surfactant. The blood was taken at 30 minutes after to measure the concentration of mitomycin C in the blood. A control experiment was conducted with a group consisting of seven rabbits. Each of the rabbits was infused with 3 ml of an aqueous solution containing 6 mg of mitomycin C to measure its concentration in the blood.

When mitomycin C was used together with lung surfactant, the concentration of mitomycin C in the blood was $1.18 \pm 1.0$ μg/ml, and the other hand when mitomycin C was used alone, its concentration was $0.10 \pm 0.06$ μg/ml.

What is claimed is:

1. A composition for curing respiratory diseases, which composition is to be directly administered by inhalation or infusion into the lungs, which contains a therapeutically effective amount of a medicine for respiratory disease and naturally or artificially prepared lung surfactant in an amount sufficient to promote absorption of the medicine or to assist respiratory function, said lung surfactant being characterized by a singular surface activity which makes the surface tension of the inner surface of the alveolium vary in accordance with the expiration and inspiration and contributes to the maintenance of interalveolium functional stabilization to exercise an anti-atelectatic action and said surfactant having a minimum surface tension of 20 dyne/cm or less on a modified Wilhelmy balance.

2. The composition for curing respiratory diseases according to claim 1, wherein the composition contains 0.01 part by weight or more of lung surfactant against 1 part by weight of the medicine for respiratory disease.

3. The composition for curing respiratory diseases according to claim 1, wherein the medicine for respiratory disease is an antagonizer.

4. The composition for curing respiratory diseases according to claim 1, wherein the medicine for respiratory disease is an antiallergic drug.

5. The composition for curing respiratory disease according to claim 1, wherein the medicine for respiratory disease is an antiinflammatory drug.

6. The composition for curing respiratory diseases according to claim 1, wherein the composition is a liquid dispersion.

7. The composition for curing respiratory diseases according to claim 6 wherein water is used as a liquid dispersion medium.

8. A composition for treating respiratory diseases, which composition is to be directly administered by inhalation or infusion into the lungs, which contains a therapeutically effective amount of a medicine for respiratory disease and naturally or artificially prepared lung surfactant in an amount sufficient to promote adsorption of the medicine or to assist respiratory function, said lung surfactant being characterized by a singular surface activity which makes the surface tension of the inner surface of the alveolium vary in accordance with the expiration and inspiration and contributes to the maintenance of interalveolium functional stabilization to exercise an anti-atelectatic action and said surfactant having a minimum surface tension of 20 dyne/cm or less on a modified Wilhelmy balance, said medicine for treating respiratory diseases being an anti-cancer drug.

* * * * *